(12) United States Patent
Narita et al.

(10) Patent No.: US 6,710,081 B1
(45) Date of Patent: Mar. 23, 2004

(54) ERECTION INSUFFICIENCY REMEDIES

(75) Inventors: Masami Narita, Osaka (JP); Kouzou Yoshida, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 23 days.

(21) Appl. No.: 10/110,101

(22) PCT Filed: Oct. 6, 2000

(86) PCT No.: PCT/JP00/06976

§ 371 (c)(1),
(2), (4) Date: Apr. 8, 2002

(87) PCT Pub. No.: WO01/24800

PCT Pub. Date: Apr. 12, 2001

(30) Foreign Application Priority Data

Oct. 7, 1999 (JP) .......................................... 11-287033

(51) Int. Cl.[7] ............................................... A01N 37/10
(52) U.S. Cl. ..................... 514/530; 560/121; 514/573; 514/659; 514/623; 568/189
(58) Field of Search .......................... 560/121; 514/573, 514/623, 659; 568/189

(56) References Cited

U.S. PATENT DOCUMENTS 6,462,081 B1 * 10/2002 Maruyama et al.

FOREIGN PATENT DOCUMENTS

| EP | 386901 A1 | 9/1990 |
|---|---|---|
| EP | 0 386 901 A1 | 9/1990 |
| EP | 0 737 676 A1 | 10/1996 |
| EP | 1 097 922 A1 | 5/2001 |
| JP | 63-079870 A2 | 4/1988 |
| JP | 63 079870 A2 | 4/1988 |
| WO | WO 99/02164 A1 | 1/1999 |
| WO | WO 00/003980 A1 | 1/2000 |

* cited by examiner

Primary Examiner—Paul J. Killos
(74) Attorney, Agent, or Firm—Sughrue Mion, PLLC

(57) ABSTRACT

Therapeutic agents for erectile dysfunction containing as the active ingredient prostaglandin derivatives of formula (I)

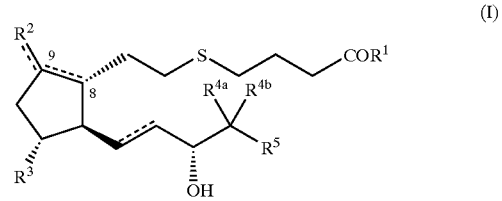

(wherein symbols have the same meanings as described in the description), nontoxic salts thereof, or cyclodextrin clathrate compounds thereof.

3 Claims, No Drawings

ERECTION INSUFFICIENCY REMEDIES

TECHNICAL FIELD

The present invention relates to a therapeutic agent for erectile dysfunction. More particularly, it relates to a therapeutic agent for erectile dysfunction containing as the active ingredient prostaglandin derivatives of general formula (I), nontoxic salts thereof or cyclodextrin clathrate compounds thereof, wherein each symbol is as defined below.

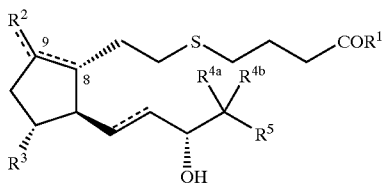

(I)

BACKGROUND ART

Male sexual dysfunction, in particular erectile dysfunction, is attributed to various causes such as aging, operation of prostate gland, injury of nerve cord, and diabetes. However, what is common in these causes is that a decrease of blood flow into the corpus cavernosum penis is the direct cause. As one of methods of treating it, administration of a vasodilator such as prostaglandin $E_1$ (hereinafter abbreviated as $PGE_1$) has been considered effective (DICP—The animal of Pharmacotherapy, 5, 363 (1991)). However, $PGE_1$ has problems that it is attended with pain (angialgia) upon administration, that the drug itself is unstable and so forth.

On the other hand, it has been found that prostaglandin $E_2$ (hereinafter, abbreviated as $PGE_2$) that has oxytocic effect also has utility for erectile dysfunction. This has made it unclear whether or not the erectile dysfunction improving action of $PGE_1$ is simply based on its vasodilating action without reservation (WO93/00894).

$PGE_2$ is known to be as a metabolite in the cascade of arachidonic acid and have various activities such as cytoprotection, oxytocic effect, algesic effect, promotion of vermicular movement of digestive tract, arousal effect, supression of gastric-acid secretion, hypotensive activity, and diuretic action.

Studies in recent years have revealed that $PGE_2$ receptors have subtypes that play different roles from each other. Currently known subtypes are roughly classified into four groups called $EP_1$, $EP_2$, $EP_3$, and $EP_4$, respectively (Negishi M. et al, J. Lipid Mediators Cell Signaling 12, 379–391 (1995)). Examination of separate roles of these receptors with compounds that bind to specific receptors and finding compounds not to bind any other subtype receptors has made it possible to obtain drugs having less side effects.

Recently, an application disclosing that a compound having an ω-chain modified with a hydroxyl group has an effect on erectile dysfunction equivalent to that of $PGE_1$ and is less irritating has been laid open to public inspection. It also describes that the compound disclosed therein is $EP_2$-specific (cf., WO00/02164).

Furthermore, the compound of the present invention represented by formula (I-1) hereinbelow is the compound described in Example 3 in the specification of International Publication No. WO00/03980. Further, alkyl esters of this compound are described in other examples of the publication.

DISCLOSURE OF THE INVENTION

The inventors of the present invention have made extensive study with a view to finding a compound that has erectile dysfunction improving effect equivalent to or higher than $PGE_1$ and $PGE_2$ and has less side effects. As a result, they have found that the compounds of the present invention meet the object and attained the present invention.

The compounds of the present invention specifically bind to subtype $EP_4$ receptor but do not almost bind to other subtypes $EP_1$, $EP_2$, $EP_3$ and the like. Therefore, the compounds of the present invention do not have algesic action which may be attributed to $EP_1$, uterine relaxation which may be attributed to $EP_2$, oxytocic action which may be attributed to $EP_3$, and the like and hence they are drugs free of influences on these actions. In addition, as will be apparent from the experiments shown hereinbelow, the compounds of the present invention exhibit effects equivalent to those of $PGE_1$, whose usefulness has already been recognized, so that they are useful as therapeutic agents for erectile dysfunction having less side effects. Furthermore, the compounds of the present invention are applicable to improving of female sexual function. Although some of the compounds of the present invention are specifically disclosed in the specification of International Publication No. WO00/03980, it has not been known that the compounds are effective to erectile dysfunction.

The present invention relates to a therapeutic agent for erectile dysfunction containing as the active ingredient one or more compounds selected from prostaglandin derivatives of formula (I)

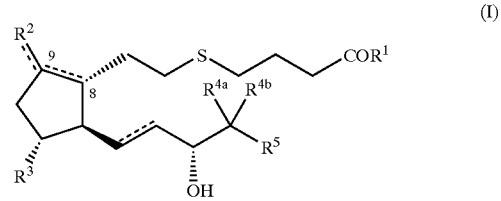

(I)

(wherein $R^1$ represents a hydroxy, $C_{1-6}$ alkyloxy or $NR^6R^7$ group (where $R^6$ and $R^7$ independently represent hydrogen or $C_{1-4}$-alkyl), $R^2$ represents an oxo, halogen, or O—$COR^8$ group (where $R^8$ represents $C_{1-4}$-alkyl, phenyl or phenyl($C_{1-4}$-alkyl)), $R^3$ represents hydrogen or hydroxy, $R^{4a}$ and $R^{4b}$ independently represent hydrogen or $C_{1-4}$-alkyl, $R^5$ represents a phenyl group substituted with the following group or groups:
  i) one to three of
    $C_{1-4}$-alkyloxy-$C_{1-4}$-alkyl,
    $C_{2-4}$-alkenyloxy-$C_{1-4}$-alkyl,
    $C_{2-4}$-alkynyloxy-$C_{1-4}$-alkyl,
    $C_{3-7}$-cycloalkyloxy-$C_{1-4}$-alkyl,
    $C_{3-7}$-cycloalkyl($C_{1-4}$-alkyloxy)-$C_{1-4}$-alkyl,
    phenyloxy-$C_{1-4}$-alkyl,
    phenyl-$C_{1-4}$-alkyloxy-$C_{1-4}$-alkyl,
    $C_{1-4}$-alkylthio-$C_{1-4}$-alkyl,
    $C_{2-4}$-alkenylthio-$C_{1-4}$-alkyl,
    $C_{2-4}$-alkynylthio-$C_{1-4}$-alkyl,
    $C_{3-7}$-cycloalkylthio-$C_{1-4}$-alkyl,
    $C_{3-7}$-cycloalkyl($C_{1-4}$-alkylthio)-$C_{1-4}$-alkyl
    phenylthio-$C_{1-4}$-alkyl, or
    phenyl-$C_{1-4}$-alkylthio-$C_{1-4}$-alkyl, ii) $C_{1-4}$-alkyloxy-$C_{1-4}$-alkyl and $C_{1-4}$-alkyl,
   $C_{1-4}$-alkyloxy-$C_{1-4}$-alkyl and $C_{1-4}$-alkyloxy,
   $C_{1-4}$-alkyloxy-$C_{1-4}$-alkyl and hydroxy,
   $C_{1-4}$-alkyloxy-$C_{1-4}$-alkyl and halogen,
   $C_{1-4}$-alkylthio-$C_{1-4}$-alkyl and $C_{1-4}$-alkyl,
   $C_{1-4}$-alkylthio-$C_{1-4}$-alkyl and $C_{1-4}$-alkyloxy,
   $C_{1-4}$-alkylthio-$C_{1-4}$-alkyl and hydroxy, or
   $C_{1-4}$-alkylthio-$C_{1-4}$-alkyl and halogen,
iii) haloalkyl, or hydroxy-$C_{1-4}$-alkyl, or
iv) $C_{1-4}$-alkyl and hydroxy;
=== represents a single bond or double bond,
provided that when $R^2$ is an O—$COR^8$ group, the 8–9 positions represent a double bond), nontoxic salts thereof, or cyclodextrin clathrate compounds thereof.

Among the compounds of formula (I), a compound of the following formula (I-1)

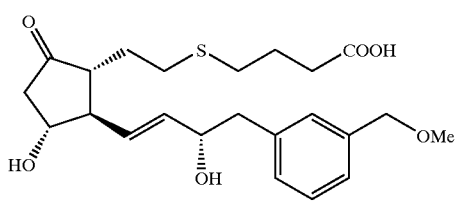

(I-1)

is preferred.

[Esters]

The compounds of formula (I) in which $R^1$ represents a hydroxy group can be converted into esters by a known method. Since esterification increases stability and absorbability of the compounds, the esters are useful as pharmaceutical preparations.

Preferred esters include alkyl esters. $C_{1-4}$-Alkyl esters are more preferred, with methyl ester being most preferred. In particular, (11α,15α,13E)-9-oxo-11,15-dihydroxy-16-(3-methoxymethylphenyl)-17,18,19,20-tetranor-5-thiaprost-13-enoic acid methyl ester, a methyl ester of the compound of formula (I-1) above is preferred.

[Salts]

The compounds of the present invention of formula (I) in which $R^1$ represents a hydroxy group can be converted into corresponding salts by a known method. The salts are preferably nontoxic and water-soluble salts. Suitable salts include alkali metal (potassium, sodium, etc.) salts, alkaline earth metal (calcium, magnesium, etc.) salts, ammonium salts, and pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine, etc.) salts. In addition, the compounds of the present invention of formula (I) can be converted into hydrates by a known method.

[Clathrate Compounds]

The compounds of formula (I) can be converted into cyclodextrin clathrate compounds by the method described in the specifications of GB 1,351,238 or GB 1,419,221 by using α-, β- or γ-cyclodextrin or mixtures thereof. Since conversion into cyclodextrin clathrate compounds increases stability and solubility in water of the compounds, the cyclodextrin clathrate compounds are convenient when they are used as drugs.

[The Method for the Preparation of Compounds of the Present Invention]

The compounds of the present invention of formula (I) can be prepared by the method described in the specification of International Publication No. WO00/03980 by the applicant. For example, the compound of formula (I-1) above and methyl ester thereof are described in Examples 3 and 1, respectively, in the aforementioned specification.

BEST MODE FOR CARRYING OUT THE INVENTION

That the compounds of the present invention can be used for the therapy of erectile dysfunction was confirmed by the following pharmacological experiments.

Intracavernosal Pressure Increasing Activity

Under anesthesia with thiopental, cannulae were indwelled in left cephalic vein (for infusion) and left femoral artery (for measuring blood pressure and heart rate) of a beagle. The epidermis was dissected from the top of penis to scrotum with an electrocautery to expose the albuguinea on the surface of the cavernous body. A cannula with a needle for measuring the inner pressure and administering a chemical was inserted into the cavernous body and (11α,15α,13E)-9-oxo-11,15-dihydroxy-16-(3-methoxymethylphenyl)-17,18,19,20-tetranor-5-thiaprost-13-enoic acid methyl ester (methyl ester of the compound of formula (I-1) above, hereinafter abbreviated as methyl ester form) was administered in four kinds of dosage, i.e., 0.2, 2.0, 20, and 200 ng. As controls, 20 ng of $PGE_1$ and physiological saline were used.

Through the cannula inserted into the corpus cavernosum penis, the chemical was injected in amounts of 100 μl and was followed by 300 μl saline injection. A difference between the maximum intra pressures up to 4 minutes from the administration and the intra pressure at the time of administration was taken as the value of intracavernosal pressure increase. The results obtained are shown in Table 1 below.

TABLE 1

| Administered Chemical | Dose (ng/100 μl) | Intracavernosal pressure increase (mmHg) |
|---|---|---|
| Methyl ester form | 0.2 | 4.3 ± 1.9 |
| Methyl ester form | 2.0 | 12.7 ± 8.7 |
| Methyl ester form | 20 | 28.3 ± 12.3 |
| Methyl ester form | 200 | 40.7 ± 16.6 |
| $PGE_1$ | 20 | 29.0 ± 12.5 |
| Physiological saline | — | 0.0 ± 0.0 |

As will be apparent from Table 1, the methyl ester of the compound of formula (I-1) increased the intracavernosal pressure dose-dependently and the effects of administration of 20 ng of the compound of the present invention and administration of 20 ng of $PGE_1$ were approximately on the same level.

[Toxicity]

It has been confirmed that the compounds of the present invention of formula (I) have sufficiently low toxicity and are sufficiently safe for use as pharmaceutical preparations. For example, the maximal tolerated dose of methyl ester of the compound of formula (I-1) was 30 mg/kg weight or more for rat intravenous administration.

INDUSTRIAL APPLICABILITY

Application to Pharmaceutical Preparations

The compounds of the present invention of formula (I) are useful for the therapy of erectile dysfunction. When used for the above-mentioned purposes, usually the compounds of the present invention of formula (I), nontoxic salts thereof, and cyclodextrin clathrate compounds thereof are locally administered in parenteral forms. Use of them in the form of prodrug provides advantages such as elimination of irritation, improved absorption, improved stability and the like.

The dosage may vary depending on age, body weight, symptom, therapeutic effect, administration method, the duration of the treatment, and the like. Usually, the dosage for an adult is in the range of from 0.1 µg to 10 mg, preferably from 0.2 mg to 5 mg, and administration is performed from once to several times a day by parenteral routes (preferably, percutaneous administration, subcutaneous administration, perurethral administration, or intravenous administration).

Of course, as described above, the dosage may vary depending on various conditions, and in some cases an amount less than the amount described above will suffice or in some cases, administration of an amount exceeding the above-mentioned range will be necessary.

When the compounds of the present invention are administered, they are used in the form of injection, external preparations such as ointments, patches for attaching to skin, suppositories and the like for parenteral administration.

The injection for parenteral administration according to the present invention includes sterile aqueous or nonaqueous solutions, suspensions and emulsions. The aqueous solutions and suspensions include, for example, distilled water for injection and saline. The nonaqueous solutions and suspensions include, for example, propylene glycol, polyethylene glycol and plant oils such as olive oil, alcohols such as ethanol, Polysorbate 80 (registered trademark) and the like. Such compositions may further contain antiseptics, humectants, emulsifiers, dispersants, stabilizers, or auxiliaries such as dissolution auxiliaries (for example, glutamic acid and aspartic acid). These can be sterilized by filtration through a bacteria-retaining filter, compounding of a germicide, or irradiation. These can be sterilized by producing a sterile solid composition and sterilizing before use or they are dissolved in sterile distilled water for injection or other solvents before they can be used.

Other compositions for parenteral administration include external liquids, ointments, liniments, patches, and suppositories, each containing one or more active ingredients.

The ointment may contain besides a base such as white vaseline, pH adjusters, surfactants, antiseptics, emulsifiers, dispersants, stabilizers, dissolution auxiliaries and so forth.

PREPARATION EXAMPLE 1

Freeze-dried Products

After mixing the following components by a conventional method, the resulting solution was sterilized by a conventional method and 1 ml portions thereof were filled in vials, respectively, and freeze-dried by a conventional method to obtain 100 vials of injection containing each 0.2 mg of the active ingredient.

(11α,15α,13E)-9-oxo-11,15-dihydroxy-16-(3-methoxymethylphenyl)-17,18,19,20-tetranor-5-thiaprost-13-enoic acid methyl ester.α-cyclodextrin 80 mg (content 20 mg)
Mannitol 5 g
Distilled water 100 ml

PREPARATION EXAMPLE 2

Ointment

The following components were mixed by a conventional method and 10 g portions thereof were filled in tubes, respectively, to obtain 100 tubes of ointment containing each 0.2 mg per 1 g of the active ingredient.

(11α,15α,13E)-9-oxo-11,15-dihydroxy-16-(3-methoxymethylphenyl)-17,18,19,20-tetranor-5-thiaprost-13-enoic acid methyl ester.α-cyclodextrin 800 mg (content 200 mg)
White vaseline 1 kg

What is claimed is:

1. A method for treatment of erectile dysfunction comprising administering to a subject in need of treatment an effective amount of one or more compounds selected from prostaglandin derivatives of formula (I)

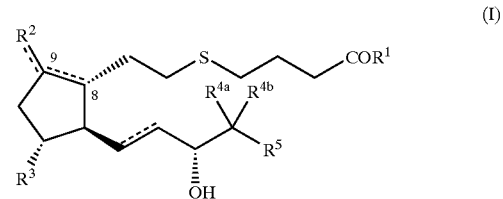

(wherein $R^1$ represents a hydroxy, $C_{1-6}$ alkyloxy or $NR^6R^7$ group (where $R^6$ and $R^7$ independently represent hydrogen or $C_{1-4}$-alkyl), $R^2$ represents an oxo, halogen, or $O-COR^8$ group (where $R^8$ represents $C_{1-4}$-alkyl, phenyl or phenyl($C_{1-4}$-alkyl)), $R^3$ represents hydrogen or hydroxy, $R^{4a}$ and $R^{4b}$ independently represent hydrogen or $C_{1-4}$-alkyl, $R^5$ represents a phenyl group substituted by the following group or groups:
  i) one to three of
    $C_{1-4}$-alkyloxy-$C_{1-4}$-alkyl,
    $C_{2-4}$-alkenyloxy-$C_{1-4}$-alkyl,
    $C_{2-4}$-alkynyloxy-$C_{1-4}$-alkyl,
    $C_{3-7}$-cycloalkyloxy-$C_{1-4}$-alkyl,
    $C_{3-7}$-cycloalkyl($C_{1-4}$-alkyloxy)-$C_{1-4}$-alkyl,
    phenyloxy-$C_{1-4}$-alkyl,
    phenyl-$C_{1-4}$-alkyloxy-$C_{1-4}$-alkyl,
    $C_{1-4}$-alkylthio-$C_{1-4}$-alkyl,
    $C_{2-4}$-alkenylthio-$C_{1-4}$-alkyl,
    $C_{2-4}$-alkynylthio-$C_{1-4}$-alkyl,
    $C_{3-7}$-cycloalkylthio-$C_{1-4}$-alkyl,
    $C_{3-7}$-cycloalkyl($C_{1-4}$-alkylthio)-$C_{1-4}$-alkyl
    phenylthio-$C_{1-4}$-alkyl, or
    phenyl-$C_{1-4}$-alkylthio-$C_{1-4}$-alkyl,
  ii) $C_{1-4}$-alkyloxy-$C_{1-4}$-alkyl and $C_{1-4}$-alkyl,
    $C_{1-4}$-alkyloxy-$C_{1-4}$-alkyl and $C_{1-4}$-alkyloxy,
    $C_{1-4}$-alkyloxy-$C_{1-4}$-alkyl and hydroxy,
    $C_{1-4}$-alkyloxy-$C_{1-4}$-alkyl and halogen,
    $C_{1-4}$-alkylthio-$C_{1-4}$-alkyl and $C_{1-4}$-alkyl,
    $C_{1-4}$-alkylthio-$C_{1-4}$-alkyl and $C_{1-4}$-alkyloxy,
    $C_{1-4}$-alkylthio-$C_{1-4}$-alkyl and hydroxy, or
    $C_{1-4}$-alkylthio-$C_{1-4}$-alkyl and halogen,
  iii) haloalkyl, or hydroxy-$C_{1-4}$-alkyl, or
  iv) $C_{1-4}$-alkyl and hydroxy;
===== represents a single bond or double bond,
provided that when $R^2$ is an $O-COR^8$ group, the 8–9 positions represent a double bond), nontoxic salts thereof, or cyclodextrin clathrate compounds thereof.

2. The method for treatment of erectile dysfunction as claimed in claim 1, wherein at least one of the one or more compounds is selected from a prostaglandin derivative of formula (I-1)

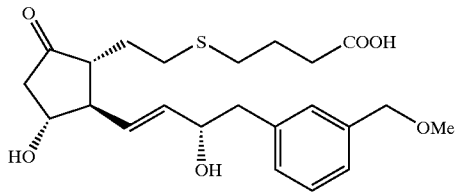

(I-1)

nontoxic salts thereof, or cyclodextrin clathrate compounds thereof.

3. The method for treatment of erectile dysfunction as claimed in claim 1, wherein at least one of the one or more compounds is (11α,15α,13E)-9-oxo-11,15-dihydroxy-16-(3-methoxymethylphenyl)-17,18,19,20-tetranor-5-thiaprost-13-enoic acid methyl ester or a α-cyclodextrin clathrate compound thereof.

* * * * *